United States Patent [19]

Ulman et al.

[11] Patent Number: 5,607,721

[45] Date of Patent: Mar. 4, 1997

[54] HOT-MELT SILICONE PRESSURE SENSITIVE ADHESIVE WITH SILOXYLATED POLYETHER WAXES AS ADDITIVES

[75] Inventors: Katherine L. Ulman, Sanford; Randall P. Sweet; Loren D. Durfee, both of Midland, all of Mich.

[73] Assignee: Dow Corning Corporation, Midland, Mich.

[21] Appl. No.: 441,509

[22] Filed: May 15, 1995

Related U.S. Application Data

[62] Division of Ser. No. 181,508, Jan. 14, 1994, Pat. No. 5,482,988.

[51] Int. Cl.$^6$ .............................. C08K 5/06; C08L 83/04; B05D 3/02; B05D 5/10

[52] U.S. Cl. ..................... 427/208.4; 524/266; 524/268; 524/588; 427/387

[58] Field of Search ................................ 427/387, 208.4; 524/266, 268, 588

[56] References Cited

U.S. PATENT DOCUMENTS

| | | | |
|---|---|---|---|
| 2,676,182 | 9/1950 | Daudt et al. | 260/448.2 |
| 2,736,721 | 2/1956 | Dexter | 260/42 |
| 2,814,601 | 11/1957 | Currie et al. | 260/29.1 |
| 2,857,356 | 10/1958 | Goodwin | 260/42 |
| 3,627,851 | 12/1971 | Brady | 260/825 |
| 3,772,247 | 11/1973 | Flaningan | 260/46.5 |
| 4,341,675 | 7/1982 | Nakamura | 524/266 |
| 4,584,355 | 4/1986 | Blizzard et al. | 525/477 |
| 4,585,836 | 4/1986 | Homan et al. | 525/477 |
| 4,591,622 | 5/1986 | Blizzard et al. | 525/477 |
| 4,655,767 | 4/1987 | Woodard et al. | 604/896 |
| 4,785,041 | 11/1988 | Antonen et al. | 524/265 |
| 4,865,920 | 9/1989 | Sweet | 428/447 |
| 5,162,410 | 11/1992 | Sweet | 524/266 |
| 5,352,722 | 10/1994 | Sweet et al. | 524/266 |

FOREIGN PATENT DOCUMENTS

| | | | |
|---|---|---|---|
| 0443759 | 2/1991 | European Pat. Off. | C09J 183/04 |
| 998232 | 7/1965 | United Kingdom . | |

OTHER PUBLICATIONS

K. L. Ulman & Chi-Long Lee, "Drug Permeability of Modified Silicone Polymers" Journal of Controlled Release, Apr. 5, 1989 pp. 273–281.

*Primary Examiner*—Karen A. Dean
*Attorney, Agent, or Firm*—Sharon K. Severance

[57] ABSTRACT

The instant invention pertains to a hot-melt pressure sensitive adhesive composition wherein the composition is comprised of a silicone pressure sensitive adhesive selected from the group consisting of a mixture of (i) a silicone resin and (ii) a silicone fluid and a condensed product of (i) and (ii); the silicone pressure sensitive adhesive exhibiting tackiness and adhesiveness; the silicone pressure sensitive adhesive being blended with (iii) from about 1 to 20 weight percent, based on the total weight of (i) and (ii), of a siloxylated polyether wax. The instant invention also encompasses method of using the composition, methods of making hot-melt silicone pressure sensitive adhesive-coated substrates, and devices made using the composition.

3 Claims, No Drawings

HOT-MELT SILICONE PRESSURE SENSITIVE ADHESIVE WITH SILOXYLATED POLYETHER WAXES AS ADDITIVES

This is a divisional of application Ser. No. 08/181,508 filed on Jan. 14, 1994, now U.S. Pat. No. 5,482,988.

BACKGROUND OF THE INVENTION

A pressure sensitive adhesive (PSA), generally, is a material which adheres to a surface with slight pressure and releases from the surface with negligible transfer of the material to the surface. Silicone pressure sensitive adhesives that are known in the art are typically solvent based adhesives; the solvents are employed primarily to reduce the silicone pressure sensitive adhesive's viscosity to a viscosity which is easily coated onto the substrate of choice, and the solvents are removed after coating.

Hot-melt pressure sensitive adhesives are those adhesives, which upon heating, melt to viscosities suitable for coating, but when cooled are generally in a flowless state. The advantages of hot-melt PSA's relative to solvent-based PSA's are known and include safety, environmental and application advantages. In addition, hot-melt PSA's have the advantage of not containing solvents which sometimes interfere with the addition of other ingredients to the PSA. Silicone pressure sensitive adhesives have been found to be preferred over other types of PSA's in many applications, especially in the medical area. Pressure sensitive adhesives have long been used to bind bandages, sensory monitors, and the like to a person's skin. In addition, silicone pressure sensitive adhesives have found use in transdermal drug delivery applications which involve the adherence of a drug-containing patch to a patient's skin.

U.S. Pat. No. 4,865,920 discloses a hot-melt PSA comprised of (i) a silicone resin, (ii) a silicone fluid and (iii) an ester having the formula R'—C(O)OR" wherein R' is a monovalent hydrocarbon radical having from 2 to 32 carbon atoms and R" is a monovalent hydrocarbon radical having from 1 to 14 carbon atoms.

Other additives, besides the esters, have recently been developed which are capable of reducing the dynamic viscosity of the PSA while also imparting other beneficial properties into the PSA. For example, U.S. Pat. No. 5,162,410 discloses a hot-melt PSA comprised of (i) a silicone resin, (ii) a silicone fluid and (iii) at least one phenyl-containing polysiloxane fluid having a viscosity at 25° C. of from about 5 to 60,000 centistoke. The compositions of U.S. Pat. No. 5,162,410 are disclosed as being more compatible with certain drugs and other organic materials than are the hot-melt PSA's of U.S. Pat. No. 4,865,920.

EP Application No. 0 443 759 discloses a hot-melt PSA comprised of (i) a silicone resin, (ii) a silicone fluid and (iii) a non-flammable hydrocarbon having weight average molecular weight of from about 300 to 1500. The compositions of EP Patent Application No. 0 443 759 are disclosed as being more compatible with certain drugs and other organic materials than are the hot-melt PSA's of U.S. Pat. No. 4,865,920.

These hot-melt compositions have been found to be inadequate for the delivery of hydrophilic drugs from transdermal drug delivery systems. There are several advantages to having a hot-melt composition that is hydrophilic. One advantage is that higher dosages of hydrophilic drugs can be employed without destroying the pressure sensitive adhesive. Another advantage is that the amount of drug released can be increased or controlled. Finally, the conditions under which a patch can be worn are greatly improved.

It is an object of this invention to provide a hot-melt silicone pressure sensitive adhesive composition that has improved hydrophilic characteristics while maintaining the pressure sensitive adhesive properties of shear, adhesion, and release.

SUMMARY OF THE INVENTION

The instant invention pertains to hot-melt pressure sensitive adhesive compositions which possess the benefits of being hot-melt adhesives and being formed of materials which are highly acceptable in topical applications. The hot-melt silicone pressure sensitive adhesive compositions of the instant invention have improved hydrophilic characteristics while retaining adhesion, shear and release.

The hot-melt silicone pressure sensitive adhesives of the instant invention are comprised of a silicone pressure sensitive adhesive selected from the group consisting of a mixture of (i) a silicone resin and (ii) a silicone fluid and a condensed product of (i) and (ii); the silicone pressure sensitive adhesive exhibiting tackiness and adhesiveness; the silicone pressure sensitive adhesive being blended with (iii) from about 1 to 20 weight percent, based on the total weight of (i) and (ii), of a siloxylated polyether wax. The instant invention also encompasses method of using the composition, methods of making hot-melt silicone pressure sensitive adhesive-coated substrates, and devices made using the composition.

THE INVENTION

The hot-melt silicone pressure sensitive adhesive of the instant invention is comprised of a silicone pressure sensitive adhesive selected from the group consisting of a mixture of (i) a silicone resin and (ii) a silicone fluid and a condensed product of (i) and (ii); the silicone pressure sensitive adhesive exhibiting tackiness and adhesiveness; the silicone pressure sensitive adhesive being blended with (iii) from about 1 to 20 weight percent, based on the total weight of (i) and (ii), of a siloxylated polyether wax.

Component (i) of the instant invention may be further described as being a soluble, hydroxyl-functional organopolysiloxane resin comprising $R_3SiO_{1/2}$ siloxane units and $SiO_{4/2}$, wherein R is selected from a monovalent radical selected from the group consisting of hydrocarbon and halogenated hydrocarbon radicals having 1 to 20 carbon atoms. By the term soluble it is meant that the organopolysiloxane can be dissolved substantially completely, in either a hydrocarbon liquid such as benzene, toluene, xylene, heptane and the like or in a silicone liquid such as cyclic or linear polydiorganosiloxanes. Preferably the resin is soluble in the silicone fluid (ii).

In the formula for resin (i), R denotes a monovalent radical selected from the group consisting of hydrocarbon and halogenated hydrocarbon radicals, preferably having less than 20 carbon atoms, and most preferably having from 1 to 10 carbon atoms. Examples of suitable R radicals include alkyl radicals, such as methyl, ethyl, propyl, pentyl, octyl, undecyl, octadecyl and others; cycloaliphatic radicals, such as cyclohexyl; aryl radicals such as phenyl, tolyl, xylyl, benzyl, alpha-methyl styryl, 2-phenylethyl and others; alkenyl radicals such as vinyl; and chlorinated hydrocarbon radicals such as 3-chloropropyl dichlorophenyl and others.

To enhance the solubility of component (i) in component (ii) it is desirable to select the predominant organic radicals of the former to match the predominant organic radicals of the latter. Preferably, at least one-third, and more preferably substantially all R radical in the formula for component (i) are methyl radicals. Examples of preferred $R_3SiO_{1/2}$ siloxane units include $Me_3SiO_{1/2}$, $PhMe_2SiO_{1/2}$ and $Ph_2MeSiO_{1/2}$ where Me denotes methyl and Ph denotes phenyl.

It is preferred that the ratio of $R_3SiO_{1/2}$ siloxane units to $SiO_{4/2}$ units has a molar ratio of 0.5 to 1.2 respectively. It is further preferred that the mole ratio of the total $R_3SiO_{1/2}$ siloxane units to $SiO_{4/2}$ units be between 0.6 and 0.8

Component (i) can be prepared by well known methods. It is preferably prepared by the silica hyrosol capping process of U.S. Pat. No. 2,676,182 to Daudt et al.; as modified by U.S. Pat. No. 3,627,851 to Brady; and U.S. Pat. No. 3,772,247 to Flannigan; each patent being incorporated herein by reference to teach how to prepare soluble organopolysiloxanes which are useful in the instant invention. The resulting resin can be used in the instant invention without further modification or it can be capped with trialkylsilyl groups to reduce the silanol content. This can be accomplished by well known methods, such as reacting the resin with a compound such as trimethylchlorosilane or hexamethyldisilazane.

Component (ii) of the instant invention is a silicone fluid, preferably a hydroxyl-terminated diorganopolysiloxane polymer. The repeat units of (ii) are $R_2SiO_{2/2}$ siloxy units wherein R is independently selected from the same hydrocarbon and halogenated radicals defined above for component (i). This component can be comprised of a single polymer or copolymer or it can be a mixture of two or more such polymers. For the purposes of the present invention, each polydiorganosiloxane polymer should have a viscosity at 25° C. of about 100 to 500,000 centipoise (cP), preferably 500 to 50,000 and most preferably 1,000 to 20,000 cP. It is preferred that at least 50%, and preferably at least 85%, of the organic radicals along the chain component (ii) are methyl radicals, which can be distributed in any manner in the diorganopolysiloxane. Further, component (ii) can comprise up to about 10 mole percent of siloxane branching sites provided it meets the above viscosity requirements.

The silicone resin is employed in amount from about 40 to 70 parts by weight in the silicone pressure sensitive adhesive, and the silicone fluid is employed from about 30 to about 60 parts by weight, wherein the total parts of the silicone resin and the silicone fluid are 100 parts. It is usually preferred that the silicone resin be employed from about 50 to 60 parts by weight, and correspondingly, the silicone fluid be employed from about 40 to 50 parts by weight, wherein the total parts by weight equals 100.

Additionally, the silicone pressure sensitive adhesive which is mixed with the siloxylated polyether wax may be selected from various known silicone pressure sensitive adhesives which may or may not be condensed products of (i) and (ii). The hot-melt silicone pressure sensitive adhesive of the instant invention do not employ solvents that are found in traditional PSA's.

One suitable class of pressure sensitive adhesives to be employed in the hot-melt composition of the instant invention consists of a mixture of a trimethylsilyl-endblocked polysilicate resin such as a silicone resin consisting of a benzene-soluble resinous copolymer containing silicon-bonded hydroxyl radicals and consisting essentially of triorganosiloxy units of the formula $R^1_3SiO_{1/2}$ and tetrafunctional siloxy units of the formula $SiO_{4/2}$ in a ratio of about 0.6 to 0.9 triorganosiloxy units for each tetrafunctional siloxy unit present in the copolymer, wherein $R^1$ is a monovalent organic radical independently selected from the group consisting of hydrocarbon radicals of from 1 to 6 carbon atoms, and (ii) a silanol-endcapped polydiorganosiloxane fluid such as a polydimethylsiloxane fluid. U.S. Pat. No. 2,736,721 to Dexter, et al. and U.S. Pat. No. 2,814,601 to Currie, et al. are hereby incorporated by reference to teach of such or similar pressure sensitive adhesive compositions.

Another class of suitable pressure sensitive adhesives to use according to the invention is that or those similar to the pressure sensitive adhesives in U.S. Pat. No. 2,857,356 to Goodwin, Jr., which is hereby incorporated by reference. U.S. Pat. No. 2,857,356 discloses a silicone pressure sensitive adhesive which consists of a mixture of ingredients comprising (i) a cohydrolysis product of a trialkyl hydrolyzable silane and alkyl silicate, wherein the cohydrolysis product contains a plurality of silicon-bonded hydroxy groups, and (ii) a linear, high viscosity organopolysiloxane fluid containing silicon-bonded hydroxy groups.

The silicone resin (i) and the silicone fluid (ii) may optionally be condensed together according to a procedure such as described in Canadian Patent 711,756 to Pail, which patent is hereby incorporated by reference. In such a condensation reaction, the silicone resin (i) and silicone fluid (ii) are mixed together in the presence of a catalytic amount of a silanol condensation catalyst, and then the silicone resin (i) and the silicone fluid (ii) are condensed, for example, by heating under reflux conditions for 1 to 20 hours. Examples of silanol condensation catalyst are primary, secondary and tertiary amines, carboxylic acids of these amines and quaternary ammonium salts.

Another class of suitable pressure sensitive adhesives to use with the siloxylated polyether waxes, according to this invention, are those compositions described in U.S. Pat. No. 4,591,622 and No. 4,584,355 to Blizzard et al., No: 4,585, 836 to Homan et al., and No. 4,655,767 to Woodard et al, hereby incorporated by reference. Generally, these pressure sensitive adhesives consist of a blend of (i) a silicone resin and (ii) a silicone fluid which are chemically treated to reduce the silicon-bonded hydroxyl content of the blend. These adhesives may optionally be condensed, as described previously, prior to the chemical treatment.

The silicone pressure sensitive adhesives useful in the instant invention should not be confused with silicone rubbers which are not useful. The silicone pressure sensitive adhesives are usually fillerless or contain low amounts, less than 5%, of fillers. On the other hand, silicone rubbers typically contain about 15 to 35% filler. Fillers are generally not required in high quantities in silicone pressure sensitive adhesives, because high quantities often cause the silicone pressure sensitive adhesives to lose tack and adhesiveness and to increase in dynamic viscosity, making it more difficult to apply a coating of the silicone pressure sensitive adhesive.

Component (iii) of the instant invention is a siloxylated polyether wax. Generally, any silicone polymer that contains a alkyl wax ($\geq C_6$) functionality and polyethylene oxide functionality will be useful in the instant invention. The siloxylated polyether waxes (iii) of the instant invention may be exemplified by silicone polymers having the general formula

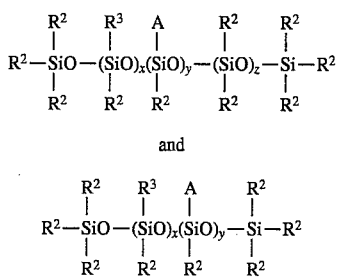

and $$R^2-SiO-(SiO)_x(SiO)_y-Si-R^2$$

(with R² groups and R³, A substituents as shown)

wherein each $R^2$ is independently selected from the group consisting of an alkyl radical having 1 to 4 carbon atoms, a phenyl radical and a hydroxyl radical; $R^3$ is an alkyl radical having 6 or more carbon atoms; A is a polyethylene oxide group selected from the group consisting of —$R_4O(CH_2CH_2O)_aR_5$ and —$R_4O(CH_2CH_2O)_a(CH_2(CH_3)CHO)_bR_5$ where $R^4$ is an alkylene radical having from 1 to 6 carbon atoms; $R^5$ is selected from the group consisting of —H and —$COCH_3$; a has a value of at least 1, and b has a value of at least 1, x has a value of greater than 0; y has a value of greater than 0; and z has a value of 1 to 100.

In the formulas for the siloxylated polyether waxes (iii), $R^2$ is selected from the group consisting of an alkyl radical having 1 to 4 carbon atoms, a phenyl radical and a hydroxyl radical. Examples of suitable $R^2$ radicals include, but are not limited to, methyl, ethyl, phenyl and hydroxyl. Preferably at least 90 mole percent of the $R^2$ radicals are methyl and more preferably all of the $R^2$ radicals are methyl.

$R^3$ in the preceding siloxylated polyether wax formulas is selected from an alkyl radicals having 6 or more carbon atoms. Examples of $R^3$ include, but are not limited to, hexyl, octyl, decyl, dodecyl, tetradecyl, hexadecyl, octadecyl, eicosyl, tetracosyl, and triacontyl.

"A" in the preceding siloxylated polyether wax formulas is a polyethylene oxide group selected from the group consisting of —$R_4O(CH_2CH_2O)_aR^5$ and —$R_4O(CH_2CH_2O)_a(CH_2(CH_3)CHO)_bR^5$ where $R^4$ is an alkylene radical having from 1 to 6 carbon atoms; $R^5$ is selected from the group consisting of —H and —$COCH_3$; a has a value of at least 1, preferably at least 20; and b has a value of at least 1. It is generally recognized by one skilled in the art that the presence of polypropylene oxide groups can be detrimental to the hydrophilicity therefore it is further preferred that when "A" is the group $R_4O(CH_2CH_2O)_a(CH_2(CH_3)CHO)_bR^5$ that b has a value of 1 to 20 and that a+b≧50. One skilled in the art will be able to readily determine the amount of polypropylene oxide that can be present without losing the hydrophilic characteristics of the wax. $R^4$ may be exemplified by, but not limited to, methylene, ethylene, propylene, butylene and others.

In the preceding siloxylated polyether wax formulas x has a value of greater than 0, preferably 1 to 70; y has a value of greater than 0, preferably 1 to 70; and z has a value of 1 to 400, preferably 1 to 100.

The polymeric structure of the siloxylated polyether waxes is not specifically limited, however, the siloxylated polyether waxes should be selected such that the melting point is greater than 37° C. but less than 200° C. Preferably the siloxylated polyether waxes useful in the instant invention should have a melting point of between 50° C. and 150° C. Siloxylated polyether waxes useful in the instant invention are known in the art.

The siloxylated polyether wax (iii) is employed in an amount of 1 to 20 weight percent, preferably from 5 to 15 weight percent, based on the total weight of the silicone resin (i) and the silicone fluid (ii).

The siloxylated polyether wax functions to decrease the dynamic viscosity of the hot-melt pressure sensitive adhesive at temperatures equal to or less than 200° C. Desirable dynamic viscosities of the wax-containing adhesives at temperatures equal to or less than 200° C. are equal to or less than 800 poise.

In general small amounts of additional ingredients may be added to the compositions of this invention. For example, antioxidants, pigments, stabilizers, fillers and others may be added as long as they do not materially alter the requirements of the desired composition. If the hot-melt silicone pressure sensitive adhesive compositions contain a filler it is desired that the filler be present in an amount of no greater than 5 weight percent based on the total weight of the silicone resin and silicone fluid.

Additionally, hot-melt PSA additives known in the art, which are effective at reducing dynamic viscosity, such as the esters described in U.S. Pat. No. 4,865,920, herein incorporated by reference, the polyphenylsiloxane fluids described in U.S. Pat. No. 5,162,410, herein incorporated by reference, the non-flammable hydrocarbons described in EP Patent Application 0 443 759 and others, may be incorporated into the hot-melt silicone pressure sensitive adhesive compositions of the instant invention.

The hot-melt silicone pressure sensitive adhesive compositions of the instant invention are prepared by merely mixing the silicone pressure sensitive adhesive comprised of siloxanes (i) and (ii) with the selected siloxylated polyether wax. The hot-melt silicone pressure sensitive adhesive is then heated to a coatable viscosity and coated on a substrate. Optionally the coated compositions may be cured. When the composition is to be cured, the composition may further contain a curing catalyst. It is preferred that such catalysts remain inactive at room temperature and temperatures reached during the hot-melt coating process. Therefore, such catalysts that either become active at temperatures higher than that of the hot-melt temperatures or become active upon exposure to another energy source such as UV light or electron beam radiation, are most suitable. The amount of catalyst employed should be sufficient to accelerate the cure of the composition. This amount can be readily determined by one skilled in the art through routine experimentation and is typically about 0.1 to 1.0 percent based on the weight of the total composition.

When using the hot-melt silicone pressure sensitive adhesive compositions of the instant invention to coat a substrate, the method comprises the steps of (a) heating the hot-melt silicone pressure sensitive adhesive composition to a coatable temperature above 25° C., (b) coating the heated hot-melt silicone pressure sensitive adhesive composition onto the substrate, and (c) cooling the coated hot-melt silicone pressure sensitive adhesive until it is in a generally non-flowing state. Typically, heating the hot-melt silicone pressure sensitive adhesive compositions of the instant invention to temperatures above 100° C., preferably 150° C., results in viscosities sutiable for coating. These coatable temperatures are low enough so that decomposition of the composition does not occur. Lower temperatures may result in coatable viscosities depending on the coating equipment used, the desired end product, and the composition of the hot-melt silicone pressure sensitive adhesive composition. For example, the thicker the layer of pressure sensitive adhesive desired, the higher the coating viscosity can be.

When the hot-melt silicone pressure sensitive adhesive compositions of the instant invention are applied to a backing or substrate, this procedure may be accomplished by using any conventional means, such as roller coating, dip coating, extrusion, knife coating, or spray coating.

The hot-melt silicone pressure sensitive adhesive compositions of the instant invention will adhere to many substrates, such as paper, cloth, glass cloth, silicone rubber, polyethylene, polyethylene terephthalate, polytetrafluoroethylene, glass, wood, metals, and skin. Therefore, there are many uses for the hot-melt silicone pressure sensitive adhesive compositions of the instant invention. Depending on the desired use, it may be desirable to apply adhesion promoters on the substrate surface upon which the hot-melt silicone pressure sensitive adhesive compositions will be placed.

The hot-melt silicone pressure sensitive adhesive compositions of the instant invention are especially suitable for assisting in delivering a bioactive agent, such as a drug to a bioactive agent-accepting substrate, such as a patient's skin. The hot-melt silicone pressure sensitive adhesive compositions of the instant invention may be employed in several types of bioactive agent delivery modes. One mode is by incorporating the bioactive agent into the hot-melt silicone pressure sensitive adhesive composition on an impermeable backing which is thereafter attached to the bioactive agent-accepting substrate to commence delivery. A second mode of delivery is achieved by attaching a permeable membrane of material to the bioactive-agent accepting substrate using the hot-melt silicone pressure sensitive adhesive composition of the instant invention, and then, contacting a reservoir of a bioactive agent to the attached permeable membrane. The bioactive agent may then pass from the reservoir through the permeable membrane and to the substrate for absorption. For this mode, a bioactive agent delivery device may be made which includes (a) a container, (b) a bioactive agent contained in the container and (c) the hot-melt silicone pressure sensitive adhesive composition of the instant invention on the container for providing a means for adhering the container to the bioactive agent-accepting substrate. Another mode of delivery comprises either the first or second mode however, the adhesive is placed on the impermeable backing or the permeable membrane along the outside perimeter of either the backing or membrane.

Due to the presence of the siloxylated polyether waxes in the hot-melt silicone pressure sensitive adhesive composition of the instant invention, the resulting adhesives have improved hydrophilic characteristics, thus allowing quicker delivery of drugs that are hydrophilic in nature. Further, the use of siloxylated polyether waxes reduces the dynamic viscosity of the PSA which improves the coatability of hot-melt silicone pressure sensitive adhesives at temperatures at or below 200° C.

So that those skilled in the art can understand and appreciate the invention taught herein, the following examples are presented, it being understood that these examples should not be used to limit the scope of this invention which is found in the claims attached hereto.

For the following examples:

RESIN A is a xylene solution of a resinous copolymeric siloxane prepared from 45 parts of sodium silicate and 20 parts $(CH_3)_3SiCl$ according to the method of U.S. Pat. No. 2,676,182 to Daudt et al., which is hereby incorporated by reference. Resin A and contains $Me_3SiO_{1/2}$ units and $SiO_{4/2}$ units in a ratio of approximately 0.75:1.0, has a nonvolatile content (NVC) of typically 69 to 71%, an acid number in the range of 0.3 to 1.4, a viscosity in the range of 90 cSt at 25° C., and a silicon-bonded hydroxyl content of about 2.5 weight percent at 100% NVC.

FLUID A is a hydroxyl-endblocked polydimethylsiloxane fluid having a viscosity of about 13,500 cP at 25—C.

PSA 1 was prepared by mixing 27.2 parts Fluid A, 47.5 parts Resin A and 11.6 parts xylene. The mixture was heated to 115° C. and anhydrous ammonia was passed through the mixture to promote silanol condensation. Water produced from the condensation was continuously driven off until the desired viscosity was attained. The ammonia was then discontinued. 13.6 parts of hexamethyldisilazane was then added to cap the residual silanol and render the product non-reactive. The resulting product was stripped and devolatized to 99% NVC to form the PSA.

PSA 2 was prepared by mixing 15.7 parts Fluid A, 31.1 parts Resin A and 6.7 parts xylene. The mixture was heated to 115° C. and anhydrous ammonia was passed through the mixture to promote silanol condensation. Water produced from the condensation was continuously driven off until the desired viscosity was attained. The ammonia was then discontinued. Nine (9.0) parts of hexamethyldisilazane was then added to cap the residual silanol and render the product non-reactive. The resulting product was stripped to remove volatiles. 15 weight parts of 1,000 cSt polydimethylsiloxane fluid was then added to produce the PSA.

PSA 3 was prepared by mixing 31.5 parts Fluid A, 55 parts Resin A and 13.5 parts xylene. The mixture was heated to 115° C. and anhydrous ammonia was passed through the mixture to promote silanol condensation. Water produced from the condensation was continuously driven off until the desired viscosity was attained. The ammonia was then discontinued. 7 weight parts of 100 cSt polydimethylsiloxane fluid was then added. The resulting product was stripped to remove volatiles to 99% NVC.

WAX 1 is a siloxylated polyether wax having the formula

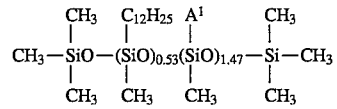

where $A^1$ is $—(CH_2)_3O(CH_2CH_2O)_{32}COCH_3$. Wax 1 has a melting point of 45° C.

WAX 2 is a siloxylated polyether wax having the formula

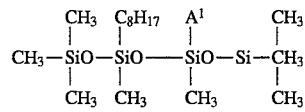

where $A^1$ is $—(CH_2)_3O(CH_2CH_2O)_{32}COCH_3$. Wax 2 has a melting point of 37° C.

WAX 3 is a siloxylated polyether wax having the formula

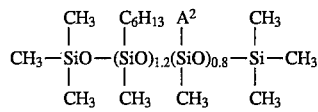

where $A^2$ is $—(CH_2)_{30}(CH_2CH_2O)_{24}COCH_3$. Wax 3 has a melting point of 36° C.

WAX 4 is a siloxylated polyether wax having the formula

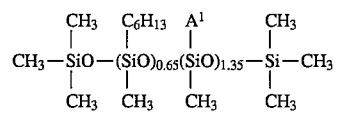

where $A^1$ is $—(CH_2)_3O(CH_2CH_2O)32COCH_3$. Wax 4 has a melting point of 43° C.

WAX 5 is a siloxylated polyether wax having the formula

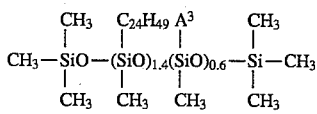

where $A^3$ is $-(CH_2)_3O(CH_2CH_2O)100COCH_3$. Wax 5 has a melting point of 55° C.

The physical properties of release, adhesion and shear were measured on the hot-melt silicone pressure sensitive adhesives Measurements were obtained by testing a one inch wide polyester tape having a silicone pressure sensitive adhesive thereon. The hot-melt silicone pressure sensitive adhesives of the instant invention were cast to yield a 2 mil thickness dry adhesive on "SCOTCH-PAK" 1022 Release liner, a polyester film coated with a release coating available from 3M Company, St. Paul, Minn. After coating, a "MYLAR" polyester film was adhered to each casted sample with a 4.5 lb. rubber transfer roller.

The laminate was then cut into one-inch wide strips with the use of a one-inch tape specimen cutter received from the Pressure Sensitive Tape Counsel. The following properties were then measured:

RELEASE: The release values were obtained by stripping the tape from the SCOTCH-PAK 1022 Release Liner at a rate of 40 inches/minute at an angle of 180° while attached to a tensile testing machine. An average value over the entire Length of the liner was recorded. Release values of less than 50 gm/cm are considered acceptable.

ADHESION: The adhesion values were obtained as follows. The tapes having the silicone PSA composition thereon were adhered to a stainless steel panel with a 4.5 lb. roller and allowed to rest for 20 minutes. The adhesion measurements were obtained by stripping each tape from the panel at a rate of 12 inches/minute at an angle of 180° while attached to a tensile testing machine. Desirable values range between about 100 and about 2000 gm/cm.

SHEAR: Shear values were measured by cutting three strips of the prepared laminates 2.5 cm wide and 7.5 cm in length. A 3.5 cm wide by 5.0 cm long strip of MYLAR is applied to the adhesive strip so as to provide an overlap of 2.5 cm in lengthwise direction. These are laminated using a 4.5 lb. roller and allowed to equilibrate for 20 minutes. The specimen is mounted in the jaws of an Instron Model 1122 Tensometer, available from Instron Corporation, and pulled at a speed of 0.5 cm/min. and the peak load required to shear and separate the laminate is recorded in $Kg/6.25\ cm^2$. Desirable values range between 4 and 25 $kg/6.25\ cm^2$.

WATER SWELL: 5 to 7 gram samples of the adhesive were hot pressed between release liner to yield a dry adhesive film of 0.130 inch thickness at 125° C. Once cooled, the samples were weighed and placed in a petri dish lined with release liner. The samples were then covered with distilled water for 24 hours. The samples were removed and air-blown dried to remove surface water. The samples were then weighed again to determine the water weight gain. The samples were then returned to the water and the procedure repeated at 48 hours. A positive water weight gain is desired.

DYNAMIC VISCOSITY ($n^*$), ELASTIC STORAGE MODULI (G') and FLUID LOSS MODULI (G"): The dynamic viscosity, elastic storage moduli and fluid loss moduli were measured on the adhesive compositions using a Rheometrics Dynamic Spectrometer, Model RDS2, available from Rheometrics, Piscataway N.J., and running a temperature sweep on 4 gram samples of 1 mm thickness and operating the tester at a frequency of 100 radians/sec. at a 1% strain using a 50 mm cup and plate. Desirable dynamic viscosities ($n^*$) should be less than or equal to 800 poise at or below 200° C.

ELASTIC STORAGE MODULI (G'): Elastic storage modulus is related to die swell and elastic memory. The higher the die swell, the smaller the size of an orifice required for a given coating thickness. Therefore, the lower the elastic storage modulus, the better, as it is then easier to coat onto a substrate. Tests similar to those run in these examples are described in ASTM 4065-82. Desirable storage modulus values should be less than 45,000 dynes/$cm^2$ at or below 200° C.

EXAMPLES 1–10

In Examples 1–5, 7 and 9 the hot-melt silicone pressure sensitive adhesives compositions were prepared by mixing the compositions indicated in Table 1 at 100° C. until homogeneously mixed and then allowing the mixture to cool to room temperature. Examples 6, 8, and 10 are provided to show the properties of the various silicone pressure sensitive adhesives without the siloxylated polyether waxes.

TABLE 1

| Example # | PSA Type Employed | Wax Employed | Weight % Wax* |
|---|---|---|---|
| 1 | 1 | 1 | 10% |
| 2 | 1 | 2 | 10% |
| 3 | 1 | 3 | 10% |
| 4 | 1 | 4 | 10% |
| 5 | 1 | 5 | 10% |
| 6 | 1 | none | 0% |
| 7 | 2 | 5 | 10% |
| 8 | 2 | none | 0% |
| 9 | 3 | 5 | 10% |
| 10 | 3 | none | 0% |

*Based on the total weight of the silicone fluid and silicone resin in the PSA composition.

As shown in Table 2, these adhesives were evaluated for physical properties of release (g/cm), adhesion (g/cm), shear ($Kg/6.25cm^2$) and water swell (%, 24 and 48 hr.). Release values ranged between 4 and 24 g/cm and all samples were within the acceptable range of less than or equal to 50 gm/cm. Adhesion values ranged between 0 and 350 g/cm and samples 4, 5, 7 and 9 were within the acceptable range of 100–2,000 gm/cm. Shear values ranged from 0 to 11.6 $Kg/2.5cm^2$ and samples 5 and 7 were within the acceptable range of 5 to 25 $kg/6.25\ cm^2$. All of the samples showed a positive water swell which indicates that the PSA's are hydrophilic in nature. These results show that the addition of siloxylated polyether waxes to the PSA's does not adversely affect the physical properties of the PSA's.

TABLE 2

| Example # | Release g/cm | Adhesion g/cm | Shear Kg | Water Swell % | |
|---|---|---|---|---|---|
| | | | | 24 hrs | 48 hrs |
| 1 | 14 | 23 | 0.7 | 2.4 | 2.8 |
| 2 | 10 | 0 | 0.0 | 1.4 | 2.0 |
| 3 | 25 | 3 | 0.7 | 1.6 | 2.3 |
| 4 | 4 | 299 | 4.1 | 1.4 | 2.4 |
| 5 | 7 | 347 | 11.6 | 1.9 | 2.7 |
| 6 | 4 | 597 | 13.5 | — | 0.4 |
| 7 | 6 | 184 | 5.0 | 1.2 | 1.9 |
| 8 | 16 | 206 | 8.0 | 0.03 | 0.15 |
| 9 | 5 | 331 | 3.0 | 3.3 | 4.4 |
| 10 | 13 | 310 | 4.5 | 0.04 | 0.2 |

Results of dynamic viscosity, elastic storage moduli and fluid loss moduli are given in Table 3. Decreased dynamic viscosity values are desirable to improve coatability without solvents. Each sample containing the siloxylated polyether wax demonstrated the desirable decreasing dynamic viscosity in comparison to the control PSA.

TABLE 3

| Example | 50° C. | | | 200° C. | | |
|---|---|---|---|---|---|---|
| # | G' | G" | N* | G' | G" | N* |
| 1 | 640,000 | 180,000 | 6,600 | 33,000 | 44,000 | 550 |
| 2 | 640,000 | 190,000 | 6,600 | 37,000 | 49,000 | 620 |
| 3 | 630,000 | 190,000 | 6,600 | 31,000 | 42,000 | 510 |
| 4 | 670,000 | 180,000 | 6,900 | 20,000 | 28,000 | 350 |
| 5 | 560,000 | 210,000 | 5,900 | 25,000 | 35,000 | 460 |
| 6 | 702,500 | 148,800 | 7,180 | 84,500 | 92,400 | 1250 |
| 7 | 480,000 | 1,000,000 | 12,000 | 7,800 | 17,000 | 190 |
| 8 | 550,000 | 1,500,000 | 16,000 | 12,000 | 29,000 | 310 |
| 9 | * | * | * | * | * | * |
| 10 | 340,000 | 490,000 | 66,000 | 6,000 | 18,000 | 190 |

*Unable to compress material between plates to 1 mm gap, no test run.

What is claimed is:

1. A method of coating a hot-melt silicone pressure sensitive adhesive composition onto a substrate, comprising:

(a) preparing a hot-melt silicone pressure sensitive adhesive by mixing together (I) a silicone pressure sensitive adhesive selected from the group consisting of a mixture of (i) a hydroxyl-functional organopolysiloxane resin comprising $R_3SiO_{1/2}$ siloxane units and $SiO_{4/2}$, wherein R is selected from a monovalent radical selected from the group consisting of hydrocarbon and halogenated hydrocarbon radicals having 1 to 20 carbon atoms and (ii) a hydroxyl-terminated diorganopolysiloxane polymer containing repeat units of $R_2SiO_{2/2}$ siloxy units wherein R is independently selected from a monovalent radical selected from the group consisting of hydrocarbon and halogenated hydrocarbon radicals having 1 to 20 carbon atoms; and a condensed product of (i) and (ii); and (II) from about 1 to 20 weight percent, based on the total weight of (I) of a siloxylated polyether wax (b) heating the hot-melt silicone pressure sensitive adhesive to a coatable temperature of between about 85° C. and 200° C.;

(c) coating the hot-melt silicone pressure sensitive adhesive onto a substrate; and (d) cooling the hot-melt silicone pressure sensitive adhesive until it is in a non-flowing state.

2. The method of coating as claimed in claim 1 wherein the hot-melt silicone pressure sensitive adhesive is heated to a coatable temperature of between 150° C. to 200° C.

3. The method of coating as claimed in claim 1 wherein the substrate is selected from the group consisting of paper, cloth, glass cloth, silicone rubber, polyethylene, polyethylene terephthalate, polytetrafluoroethylene, glass, wood, metals, and skin.

* * * * *